(12) United States Patent
Salvermoser et al.

(10) Patent No.: US 11,141,042 B2
(45) Date of Patent: Oct. 12, 2021

(54) METHOD FOR PRODUCING AN ENDOSCOPE AND SUCH AN ENDOSCOPE

(71) Applicant: Karl Storz SE & Co. KG, Tuttlingen (DE)

(72) Inventors: Markus Salvermoser, Tuttlingen (DE); Ewald Stihl, Geisingen (DE)

(73) Assignee: Karl Storz SE & Co. KG, Tuttlingen (DE)

(*) Notice: Subject to any disclaimer, the term of this patent is extended or adjusted under 35 U.S.C. 154(b) by 0 days.

(21) Appl. No.: 15/481,772

(22) Filed: Apr. 7, 2017

(65) Prior Publication Data

US 2017/0209021 A1    Jul. 27, 2017

Related U.S. Application Data

(63) Continuation of application No. 11/770,855, filed on Jun. 29, 2007, now abandoned.

(30) Foreign Application Priority Data

Jul. 1, 2006   (DE) .......................... 102006030521.3

(51) Int. Cl.
*A61B 1/00* (2006.01)
*A61B 1/002* (2006.01)
(Continued)

(52) U.S. Cl.
CPC ................ *A61B 1/00* (2013.01); *A61B 1/002* (2013.01); *A61B 1/0008* (2013.01);
(Continued)

(58) Field of Classification Search
CPC ............ A61B 1/00117; A61B 1/00119; A61B 1/00071; A61B 1/0011; F16C 2226/12;
(Continued)

(56) References Cited

U.S. PATENT DOCUMENTS 2,621,651 A   12/1952  Wallace
4,237,871 A   12/1980  Bonnet
(Continued)

FOREIGN PATENT DOCUMENTS

DE        7338410 U    5/1974
DE       19713275 A1   1/1998
(Continued)

OTHER PUBLICATIONS

German Search Report Application No. DE 10 2006 030 521.3 dated Jan. 31, 2007 4 pages.
(Continued)

*Primary Examiner* — David P Bryant
*Assistant Examiner* — Nirvana Deonauth
(74) *Attorney, Agent, or Firm* — Whitmyer IP Group LLC

(57) ABSTRACT

A method for producing an endoscope that includes an endoscope head and an optic tube, including the steps of providing the endoscope head, providing the optic tube, and pushing a proximal end area of the optic tube into a distal end area of the endoscope head. The distal end area of the endoscope head is press-fitted with the proximal end area of the optic tube.

20 Claims, 9 Drawing Sheets

(51) Int. Cl.
*G02B 23/24* (2006.01)
*F16L 13/14* (2006.01)

(52) U.S. Cl.
CPC ........ *A61B 1/0011* (2013.01); *A61B 1/00064* (2013.01); *A61B 1/00071* (2013.01); *A61B 1/00096* (2013.01); *F16L 13/147* (2013.01); *G02B 23/2476* (2013.01)

(58) Field of Classification Search
CPC .............. F16C 2226/50; F16C 2226/52; F16C 2226/70; B23P 11/005; A61M 25/0014; A61M 25/1036
See application file for complete search history.

(56) References Cited

U.S. PATENT DOCUMENTS

| | | | |
|---|---|---|---|
| 4,390,012 A | 6/1983 | Mizumoto | |
| 4,732,139 A | 3/1988 | Kawashima et al. | |
| 4,779,613 A | 10/1988 | Hashiguchi et al. | |
| 5,341,566 A * | 8/1994 | Quitschau | B21D 39/06 |
| | | | 29/890.035 |
| 5,408,992 A | 4/1995 | Hamlin et al. | |
| 5,575,757 A | 11/1996 | Kennedy et al. | |
| 5,954,637 A | 9/1999 | Francis | |
| 6,419,628 B1 * | 7/2002 | Rudischhauser | A61B 1/00135 |
| | | | 600/130 |
| 2002/0133058 A1 | 9/2002 | Calderwood | |
| 2004/0077928 A1 | 4/2004 | Moriyama | |
| 2006/0069307 A1 | 3/2006 | Boulais | |
| 2006/0208479 A1 * | 9/2006 | Ozaka | B21D 39/06 |
| | | | 285/124.3 |
| 2006/0236521 A1 * | 10/2006 | Ikawa | B21D 39/06 |
| | | | 29/523 |
| 2007/0074720 A1 | 4/2007 | Schwartz et al. | |

FOREIGN PATENT DOCUMENTS

JP  5897493 B2  6/1983
WO  0014443 A1  3/2000

OTHER PUBLICATIONS

European Search Report Application No. EP 07 01 2791 Completed: Oct. 26, 2007; dated Nov. 23, 2007 5 Pages.

* cited by examiner

METHOD FOR PRODUCING AN ENDOSCOPE AND SUCH AN ENDOSCOPE

CROSS-REFERENCE TO RELATED APPLICATIONS

This application is a continuation of currently pending U.S. patent application Ser. No. 11/770,855 filed Jun. 29, 2007, which claims priority of German Patent Application No. 10 2006 030 521.3 filed Jul. 1, 2006.

TECHNICAL FIELD

The invention relates to a method for producing an endoscope, the endoscope comprising an endoscope head and an optic tube. Such a method, and an endoscope produced by this method, are generally known.

BACKGROUND

Endoscopes are mainly used in minimally invasive surgery in order to examine body cavities or hollow organs. For this purpose, an endoscope comprises an endoscope head, on whose distal end an elongate endoscope shaft is mounted that comprises an optic tube. Connector pieces, for an external lighting source and irrigation/suction lines, and an eyepiece can be provided on the endoscope head. By way of the connector piece for the lighting source, light is coupled into an optical waveguide system extending through the endoscope head and the endoscope shaft and is guided to the distal end of the endoscope shaft. The endoscope also comprises an optics system for imaging purposes. The imaging optics can be made from optical fibres, rod lenses or the like, but can also include an image sensor with electrical signal transmission.

Depending on the material of the endoscope shaft, endoscopes can be made rigid or flexible. A rigid endoscope has a shaft made from a non-flexible material, for example stainless steel or metal.

To examine a cavity of the body, a distal end area of the endoscope is introduced into the latter, while the endoscope head, and the part of the endoscope shaft not inserted into the body cavity, remain outside the body.

The production of an endoscope comprises, among other things, connecting a proximal end area of the shaft to a distal end area of the endoscope head.

Known methods involve preparing the endoscope head and the optic tube of the endoscope and pushing the two parts into one another in such a way that the optic tube is received with its proximal end area in the distal end area of the endoscope head. The contact surfaces of both end areas are connected to one another by soldering, welding or adhesive bonding.

A disadvantage of these known methods is that connecting the endoscope head and the optic tube is technically very complicated. In the endoscope production process, suitable machines have to be provided that permit welding, soldering or adhesive bonding of the contact surfaces of the endoscope head and of the optic tube. Moreover, these known methods of connecting the endoscope head to the optic tube require a great deal of time. In particular, when bonding the two endoscope parts to one another, care must be taken to ensure that the optic tube and the endoscope head are held in a fixed position until the adhesive has dried.

Another disadvantage of these methods is the difficulty in keeping the optic tube and the endoscope head exactly positioned relative to one another during the production process, such that the length of the endoscope is reproducible. If the resulting overall length of the produced endoscope deviates just slightly from the desired length, this difference in length has to be taken into account in the design of the optical waveguide system and the imaging optics.

In the known production methods by means of welding and soldering; a further disadvantage is that; during the production process, heat develops in the area of the connecting site between the two endoscope parts. The heating of the material of the optic tube can cause said material to become brittle, thus reducing the strength of the optic tube in the area where it is affected by heat, with the result that the optic tube may already break under the effect of slight flexural stresses.

A further disadvantage is that, in endoscopes that are produced by the known methods, the connection between the endoscope head and the optic tube is not stable. If, during an operation, the optic tube is subjected to a considerable leverage on account of a flexural stress, it is possible that the endoscope will break at the connecting site, i.e. the welding, soldering or adhesive bonding site; between the endoscope head and the optic tube.

SUMMARY

It is therefore an object of the present invention to remedy this situation and to make available a method that is of the type mentioned at the outset and that permits a technically simple and stable connection between the endoscope head and the optic tube.

It is also an object of the present invention to make available an endoscope of the type mentioned at the outset, in which the endoscope head is of a simple construction and is connected in a stable manner to the optic tube.

According to an aspect to the invention, a method for producing an endoscope, the endoscope comprising an endoscope head and an optic tube, is provided, the method comprising the steps of providing the endoscope head, providing the optic tube, pushing a proximal end area of the optic tube into a distal end area of the endoscope head, and press-fitting the distal end area of the endoscope head with the proximal end area of the optic tube.

According to another aspect of the invention, an endoscope is provided, comprising an endoscope head and an optic tube, wherein a proximal end area of the optic tube is press-fitted with a distal end area of the endoscope head.

The method according to the invention and the endoscope according to the invention permit a technically very simple connection between the endoscope head and the optic tube. Press-fitting the two endoscope parts together advantageously requires no further auxiliaries, for example soldering tin or adhesive. Moreover, the method according to the invention can be carried out in less time than soldering, welding or adhesive bonding of the endoscope head to the optic tube. Therefore, during production of the endoscope, it is possible to omit process steps such as cooling or drying of the connecting site between the endoscope head and the optic tube.

Also, by press-fitting the optic tube with the endoscope head, which pressing operation can be carried out cold and without heating, no material weakness is caused by the effect of heat, as does occur in the case of welding or soldering.

A further advantage of the method according to the invention compared to the known methods is the fact that the connection between the optic tube and the endoscope head is stable, and remains so over the course of time. Since the two endoscope parts are pressed together, the endoscope is not sensitive to external influences, such as water. Consequently, the optic tube does not come loose, not even after a large number of cleaning processes of the endoscope, with the result that expensive repair work is avoided.

The pressing together of the endoscope head and optic tube also permits a stable connection between both parts. In this way, the endoscope advantageously withstands even considerable flexural stresses of the optic tube that generate a considerable leverage on the optic tube.

In a preferred embodiment, the proximal end area of the optic tube is press-fitted by axial compressing.

This measure represents a constructionally simple pressing of the optic tube onto the endoscope head. Since the wall thickness of the optic tube is smaller than that of the endoscope head, the optic tube is more suitable for an axial compressing process than is the endoscope head for a crimping process.

In another preferred embodiment, the optic tube is held in an axially fixed position during the pressing operation, and an axial force in the direction of a distal end area of the optic tube is exerted on the proximal end area of the optic tube.

This measure has the advantage that the press-fitting of the optic tube with the endoscope head is achieved in a simple manner in that the inserted optic tube is held at the distal end of the endoscope head and an axial force, which acts in the direction of the distal end of the optic tube, is exerted on it at the same time. The proximal end area of the optic tube is thereby axially compressed and press-fitted with the endoscope head.

In another preferred embodiment, the axial force is provided by a pressing tool, in particular a mandrel.

This measure represents a technically simple possibility of generating the axial force acting on the optic tube. In contrast to the known methods, the outlay in terms of tools is much less.

In another preferred embodiment, the distal end area of the endoscope head is provided on its inside with a circumferential recess into which material of the optic tube flows with a form fit during the pressing operation.

This measure has the advantage that the optic tube is held in an axially particularly secured position in the endoscope head, because material of the optic tube engages in the recess of the endoscope head. Tensile forces and pressure forces on the optic tube in the axial direction do not lead to a change in position of the optic tube relative to the endoscope head.

In another preferred embodiment, the circumferential recess is provided as a groove extending about the full circumference.

This measure has the advantage that; because of this design of the recess, a particularly large amount of material can engage in the recess. The connection of the endoscope head to the optic tube is therefore particularly stable.

In another preferred embodiment, the distal end area of the endoscope head is provided with at least one circumferentially limited cavity into which material of the optic tube flows with a form fit during the pressing operation.

This measure has the advantage that the material pushed into the circumferentially limited cavity ensures that the optic tube cannot turn relative to the endoscope head about its longitudinal axis. In this way, the optic tube is secured against rotation in a simple manner.

In another preferred embodiment, a proximal end of the optic tube is additionally widened in a trumpet shape.

This measure has the advantage that the proximal end of the optic tube points outwards and away from the longitudinal axis of the optic tube. If, during subsequent assembly work, optical fibres are introduced through the optic tube and the endoscope head, these are advantageously prevented from damage, for example from kinking or breaking.

In another preferred embodiment, the distal end area of the endoscope head is adhesively bonded to the proximal end area of the optic tube after the pressing operation.

This measure has the advantage that the endoscope is sealed against external influences, for example water. However, in contrast to the known methods, the adhesive does not have to apply the adhesion force for the secure connection between optic tube and endoscope head, such that the adhesion site does not represent a predetermined break point.

Further advantages and features will become clear from the following description and from the attached drawing.

It will be appreciated that the aforementioned features and those still to be explained below can be used not only in the cited combinations, but also in other combinations or singly, without departing from the scope of the present invention.

BRIEF DESCRIPTION OF THE DRAWINGS

The invention is described and explained in more detail below on the basis of a number of selected illustrative embodiments and with reference to the attached drawing, in which.

DETAILED DESCRIPTION

Figure 1:
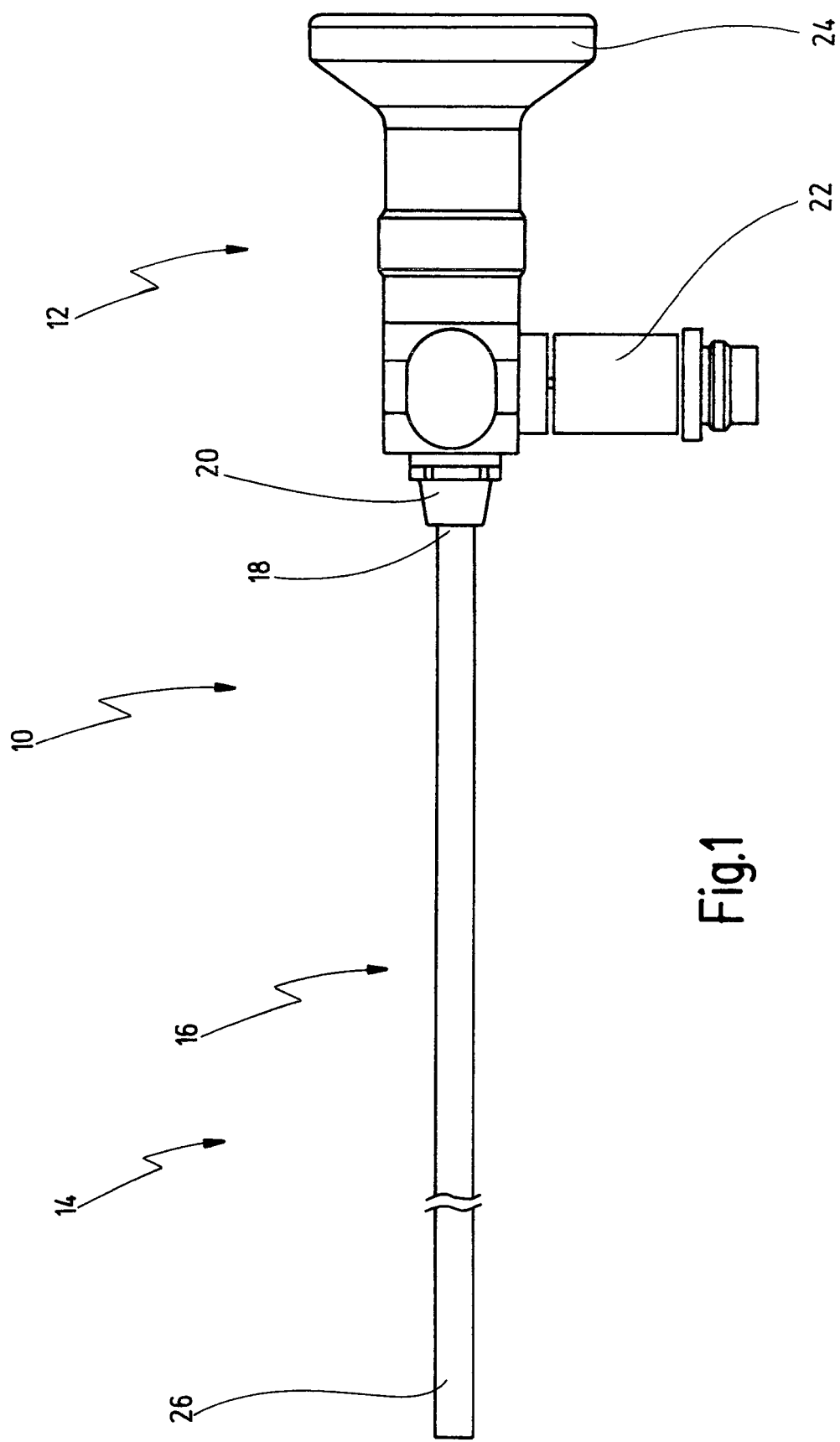
FIG. 1 shows a side view of an endoscope.

An endoscope designated by the general reference number 10 is shown in FIG. 1. The endoscope 10 comprises an endoscope head 12 and an endoscope shaft 14.

Such an endoscope 10 is used, for example, in minimally invasive surgery for examining body cavities or hollow organs. The distal end of the endoscope 10 is introduced into an opening in the body, such that at least the endoscope head 12 remains outside the body.

The endoscope shaft 14 comprises an elongate optic tube 16 whose proximal end area 18 is connected to a distal end area 20 of the endoscope head 12. The optic tube 16 is preferably designed as a cylinder-shaped hollow cylinder with a thin wall.

A connector piece 22, for an external lighting source, and an eyepiece 24 are arranged on the endoscope head 12. The endoscope 10 also accommodates an optical waveguide system that extends from the connector piece 22 to a distal end area 26 of the optic tube 16 and is made up of optical fibres. The optical waveguide system is used to illuminate an operating site within the opening in the body. The endoscope 10 also accommodates an imaging system that extends from the eyepiece 24 to the distal end area 26 of the optic tube 16. The imaging system can comprise optical fibres, rod lenses, or also an image sensor with electrical signal transmission.

The endoscope 10 is preferably rigid, the optic tube 16 being made from non-flexible materials, for example steel or metal.

Figure 2:
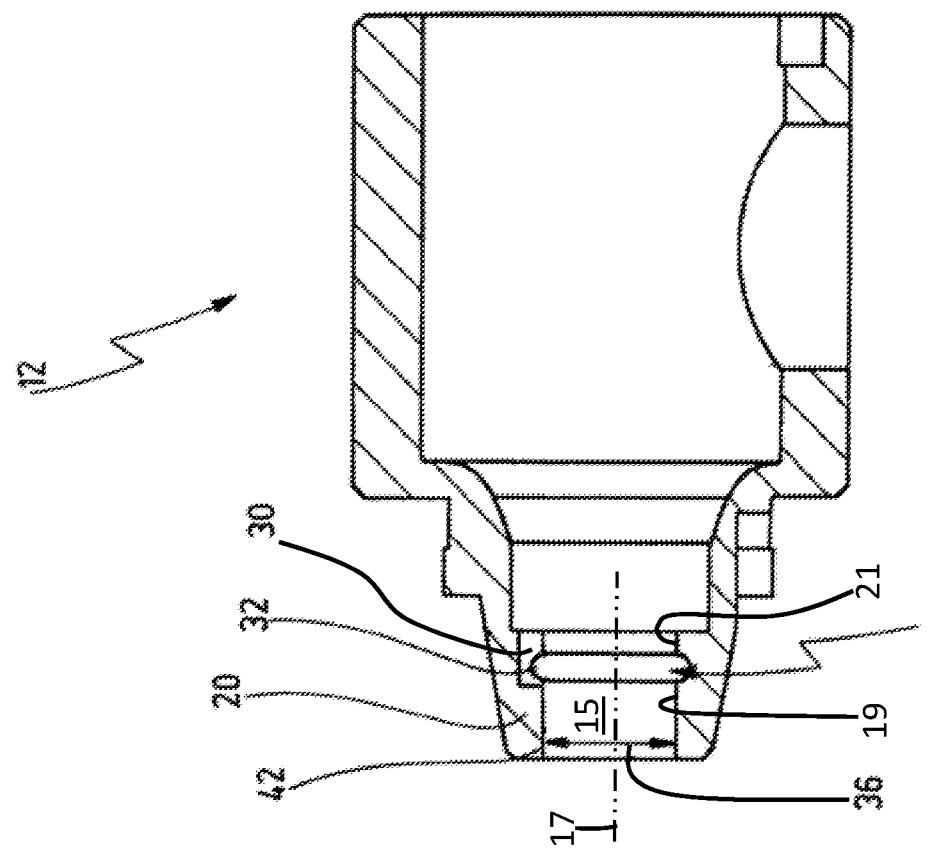
FIG. 2 shows an optic tube (in cutaway view) and an endoscope head in longitudinal section at the start of a method for producing the endoscope.
Figure 2:
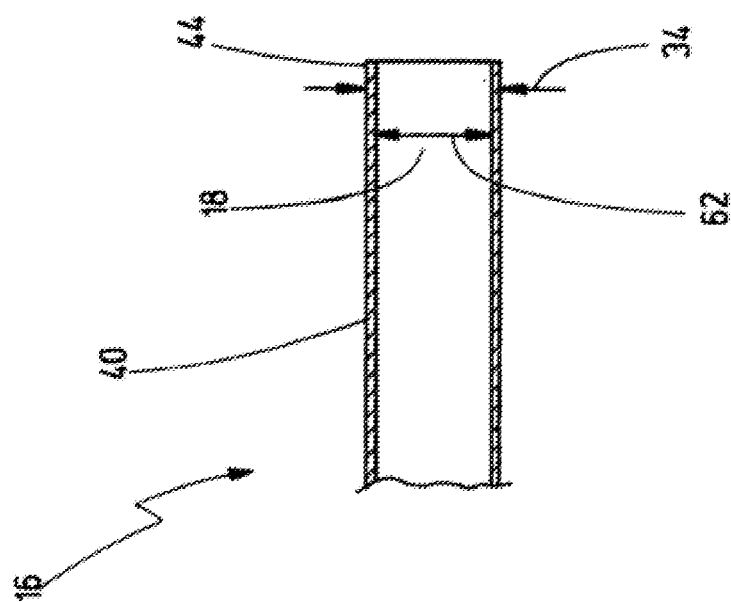

In a method for producing the endoscope 10, the optic tube 16 and the endoscope head 12 are provided in a first method step (see FIG. 2). At its distal end area 20, the endoscope head 12 has a bore 15 extending along a bore axis 17 and defining a circumferential recess 28 and at least one circumferentially limited cavity 30.

The recess 28 is preferably designed as a groove 32 that extends about the full circumference of the bore 15 in the distal end area 20 of the endoscope head 12. The cavity 30 can either be arranged directly on a part of the recess 28 or can be arranged spatially separate from the latter in the distal end area 20 of the endoscope head 12. Moreover, the cavity 30 can be set deeper in relation to the recess 28, as seen in the radial direction of the distal end area 20 of the endoscope head 12.

An external diameter 34 of the optic tube 16 is dimensioned such that it is slightly smaller than an internal diameter 36 of the bore 15 in the distal end area 20 of the endoscope head 12. The bore 15 includes a distal bore portion defined by a distal bore surface 19, and a proximal bore portion defined by a proximal bore surface 21. The recess 28 extends between the distal and proximal bore portions.

Figure 3:
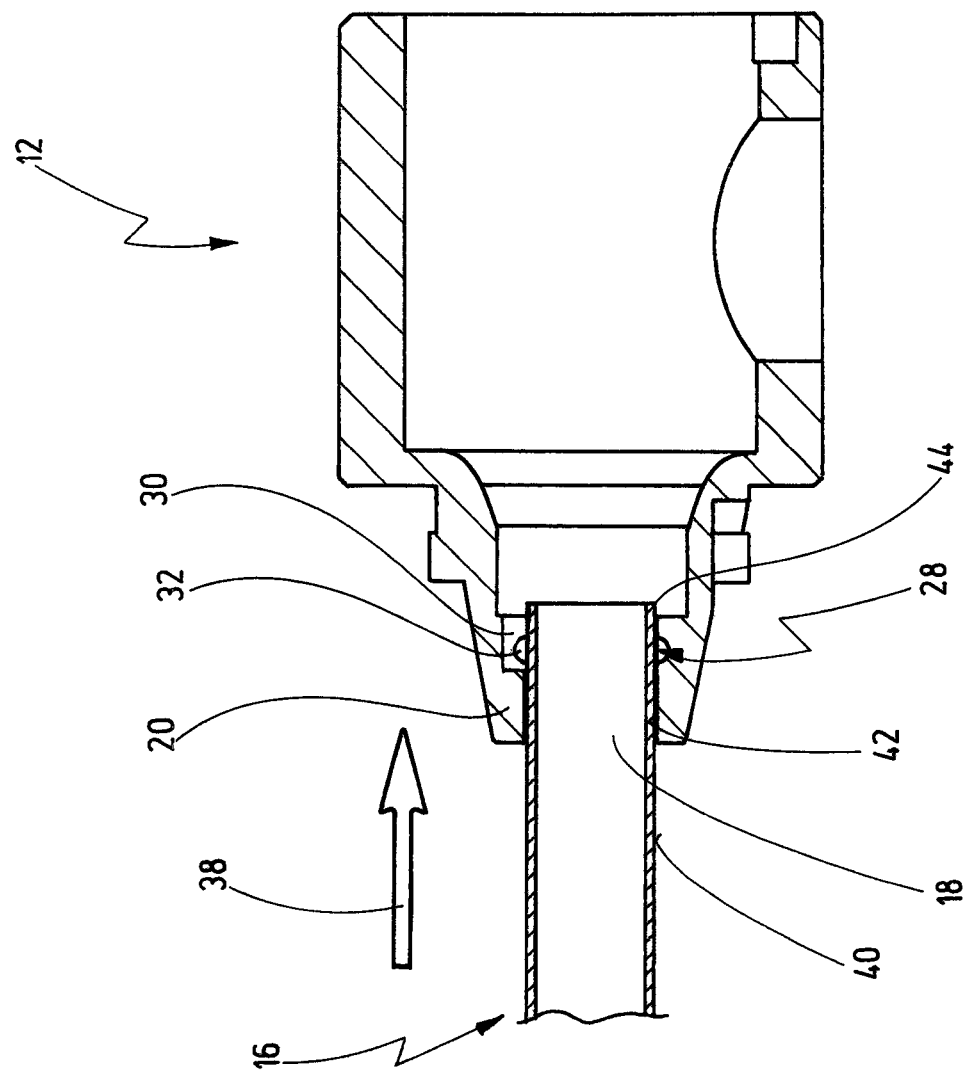
FIG. 3 shows the optic tube and the endoscope head from FIG. 2 in a further method step of the production method.

In a further method step, as is shown in FIG. 3, the proximal end area 18 of the optic tube 16 is pushed in a direction of an arrow 38 into the distal end area 20 of the endoscope head 12. In doing so, an outer surface 40 of the optic tube 16 touches an inner surface 42 of the endoscope head 12, or the outer surface 40 of the optic tube 16 is spaced slightly apart from the inner surface 42 of the distal end area 20 of the endoscope head 12. Moreover, the proximal end area 18 of the optic tube 16 is pushed so far into the distal end area 20 of the endoscope head 12 that at least a proximal end 44 of the optic tube 16 extends past the recess 28 and the cavity 30.

FIGS. 4-8 show the distal end area 20 of the endoscope head 12 and the proximal end area 18 of the optic tube 16 being pressed together.

Figure 4:
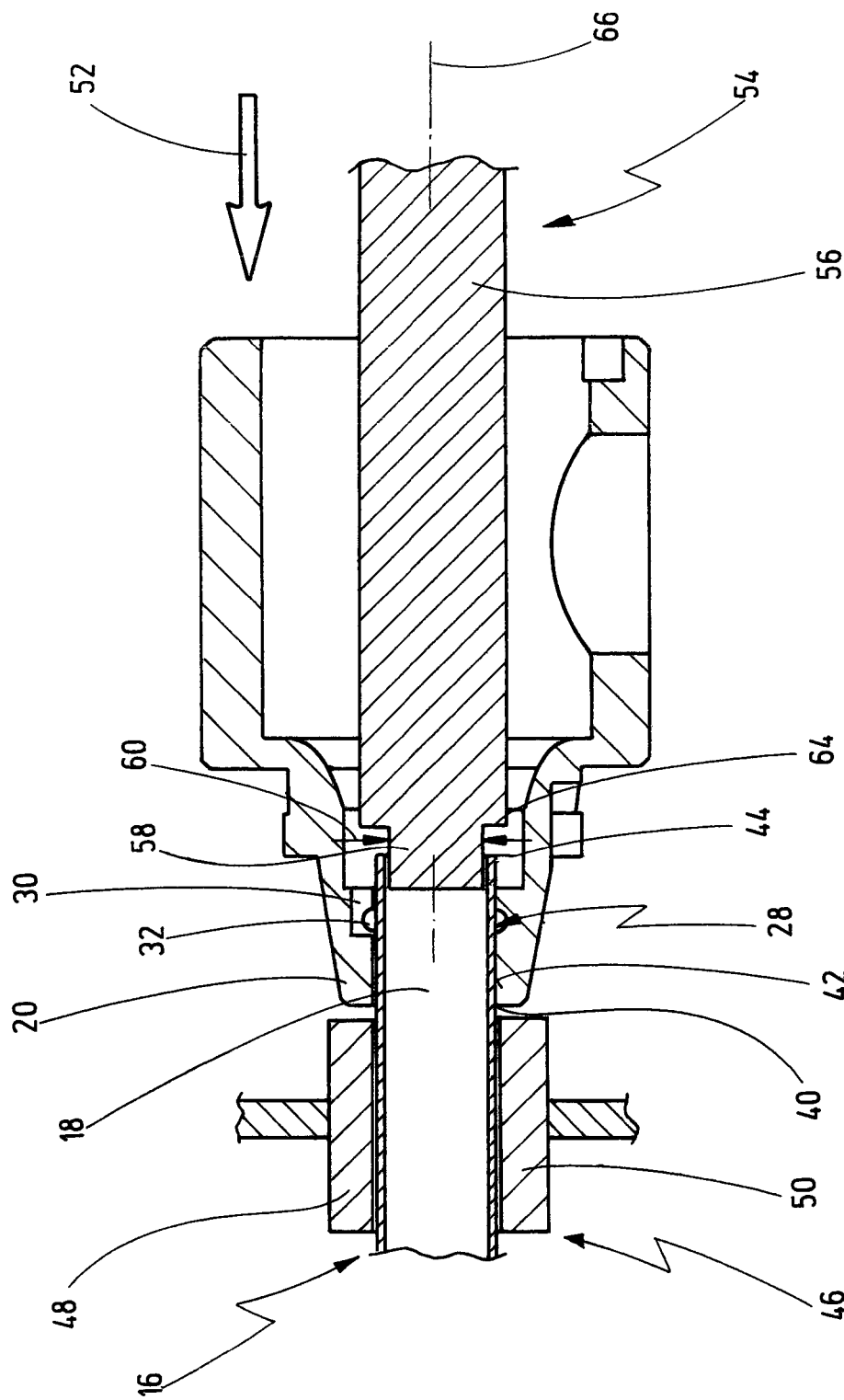
FIG. 4 shows the endoscope head and the optic tube from FIG. 3 with a pressing tool in a further method step of the production method.

The optic tube 16, whose proximal end area 18 is pushed into the distal end area 20 of the endoscope head 12, is held in an axially fixed position in respect of tensile forces and pressure forces acting in the axial direction of the optic tube 16 (see FIG. 4). For this purpose, the optic tube 16 is clamped in a holding device 46. Such a holding device 46 can, for example, have two jaws 48, 50, which engage on the outer surface 40 of the inserted optic tube 16 distally of the distal end area 20 of the endoscope head 12. The two jaws 48, 50 either touch the distal end area 20 of the endoscope head 12 or are spaced slightly apart from it. The jaws 48, 50 of the holding device 46 are shown in FIG. 4, whereas, for reasons of clarity, they are not shown in FIGS. 5-8.

An axial force is exerted on the proximal end area 18 of the optic tube 16 in the direction of an arrow 52. The axial force is generated by means of a pressing tool 54, which is guided from the proximal direction through the endoscope head 12 into the optic tube 16.

The pressing tool 54 can preferably be designed as a cylindrical mandrel 56. The pressing tool 54 narrows in a step shape at a distal end 58, such that an external diameter 60 of the distal end 58 of the pressing tool 54 is slightly smaller than an internal diameter 62 of the optic tube 16. Moreover, in the area of the step-shaped narrowing, the pressing tool 54 has a plane surface 64 that preferably extends about its full circumference and that is transverse to a longitudinal axis 66 of the pressing tool 54, and on which the proximal end 44 of the optic tube 16 comes to lie on the full circumference. The distal end 58 of the pressing tool 54 is preferably of such a length that the pressing tool 54 extends past the recess 28 and the bulge 30 when in a fully inserted state, i.e. when the plane surface 64 touches the proximal end 44 of the optic tube 16.

Figure 5:
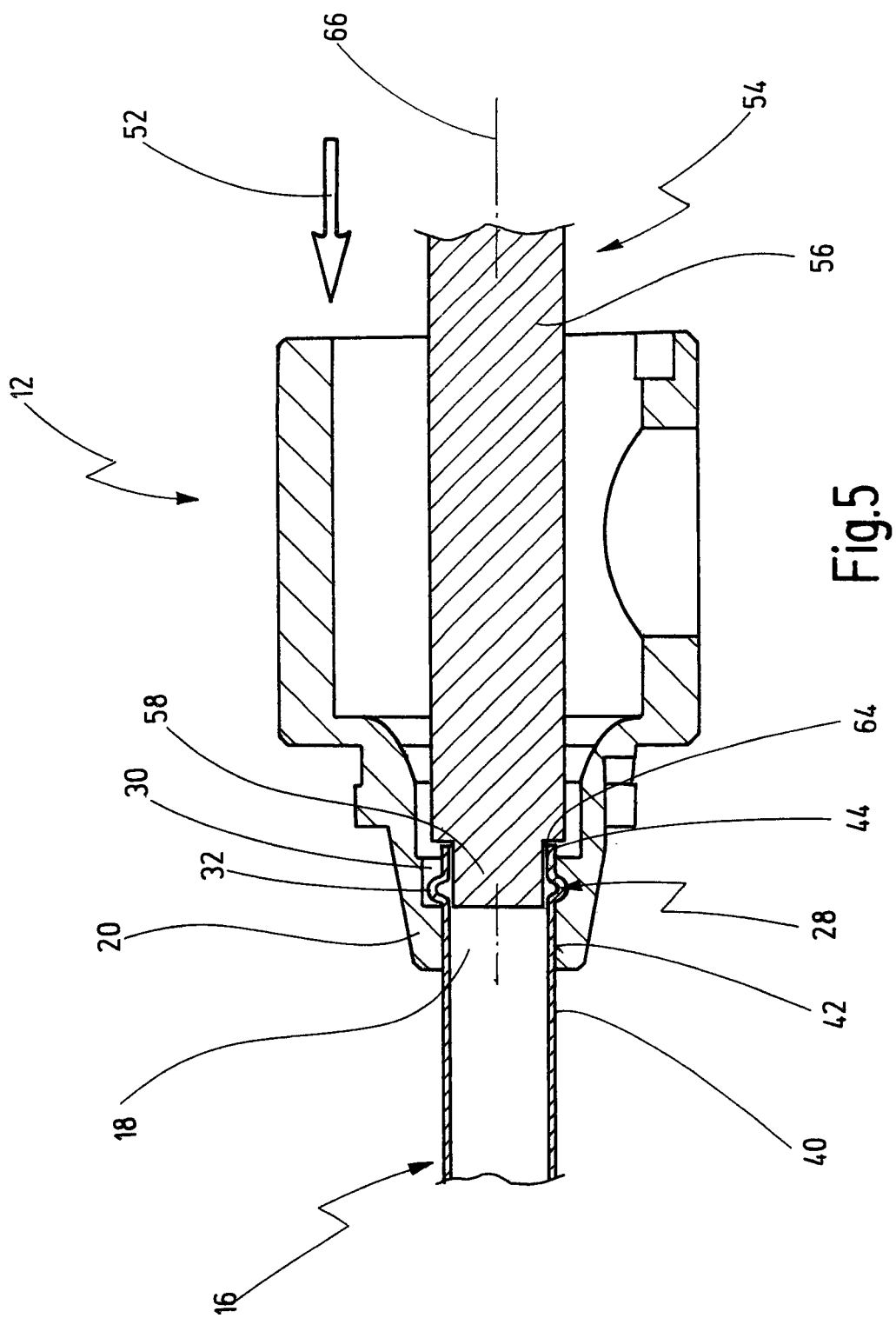
FIG. 5 shows the endoscope head, the optic tube and the pressing tool from FIG. 4 in a further method step of the production method.

As is shown in FIG. 5, the proximal end area 18 of the optic tube 16 is axially compressed by the axial force in such a way that axially compressed material is forced radially outwards. This is especially the case when the distal end 58 of the pressing tool 54 extends past the recess 28 and the cavity 30 and thus prevents a radially inwardly directed movement of the buckled material. Material of the proximal end area 18 of the optic tube 16 thus engages with a form fit in the recess 28 while the optic tube 16 is press-fitted with the endoscope head 12. The engagement of the material of the optic tube 16 into the recess 28 permits a secure axial positioning of the optic tube 16 relative to the endoscope head 12.

Figure 6:
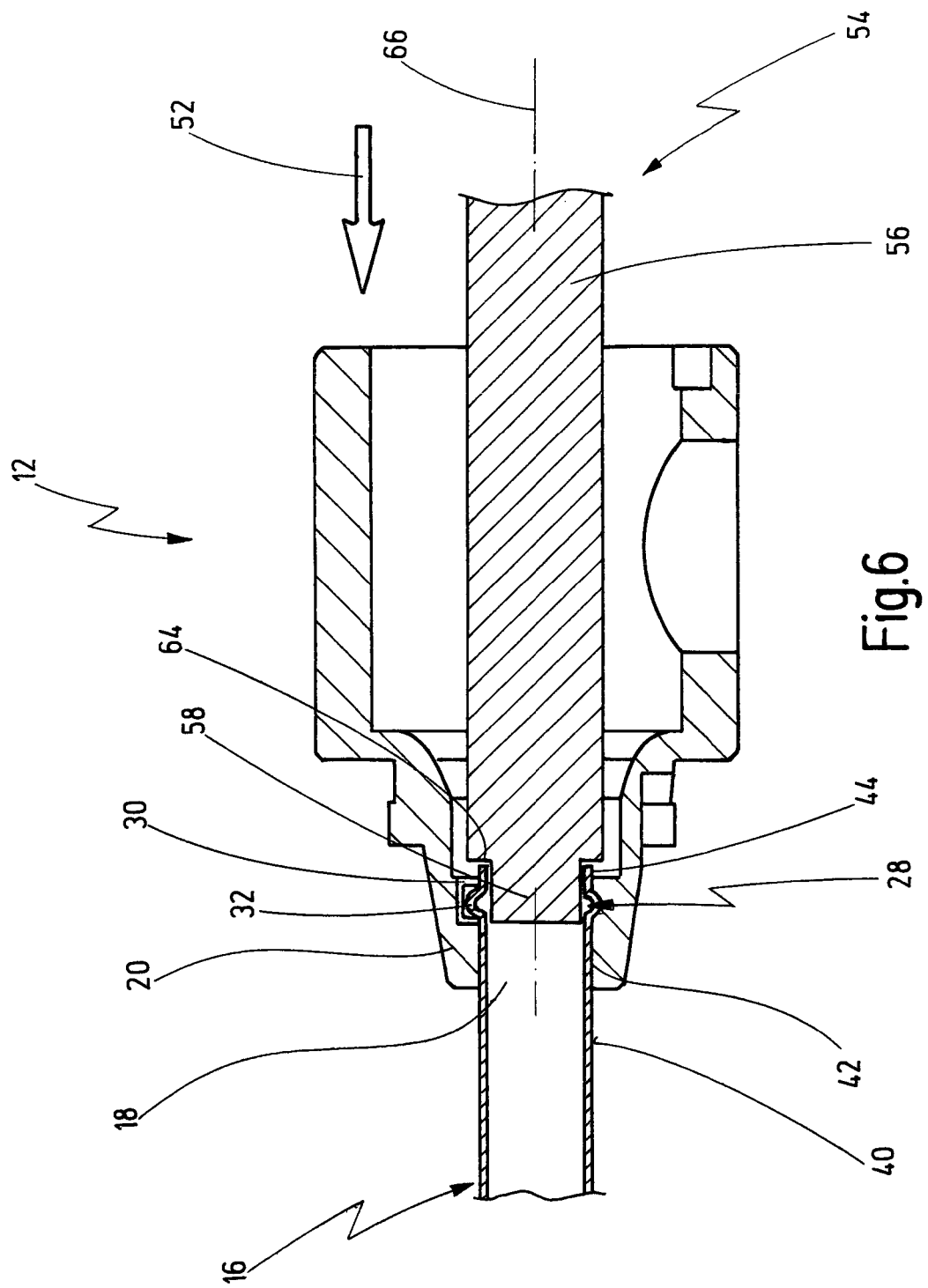
FIG. 6 shows the endoscope head, the optic tube and the pressing tool from FIG. 5 in a further method step of the production method.

The pressing action also causes material of the optic tube 16 to engage in the cavity 30 (see FIG. 6). This ensures that the optic tube 16 is not able to turn relative to the endoscope head 12 about its longitudinal axis.

Figure 7:
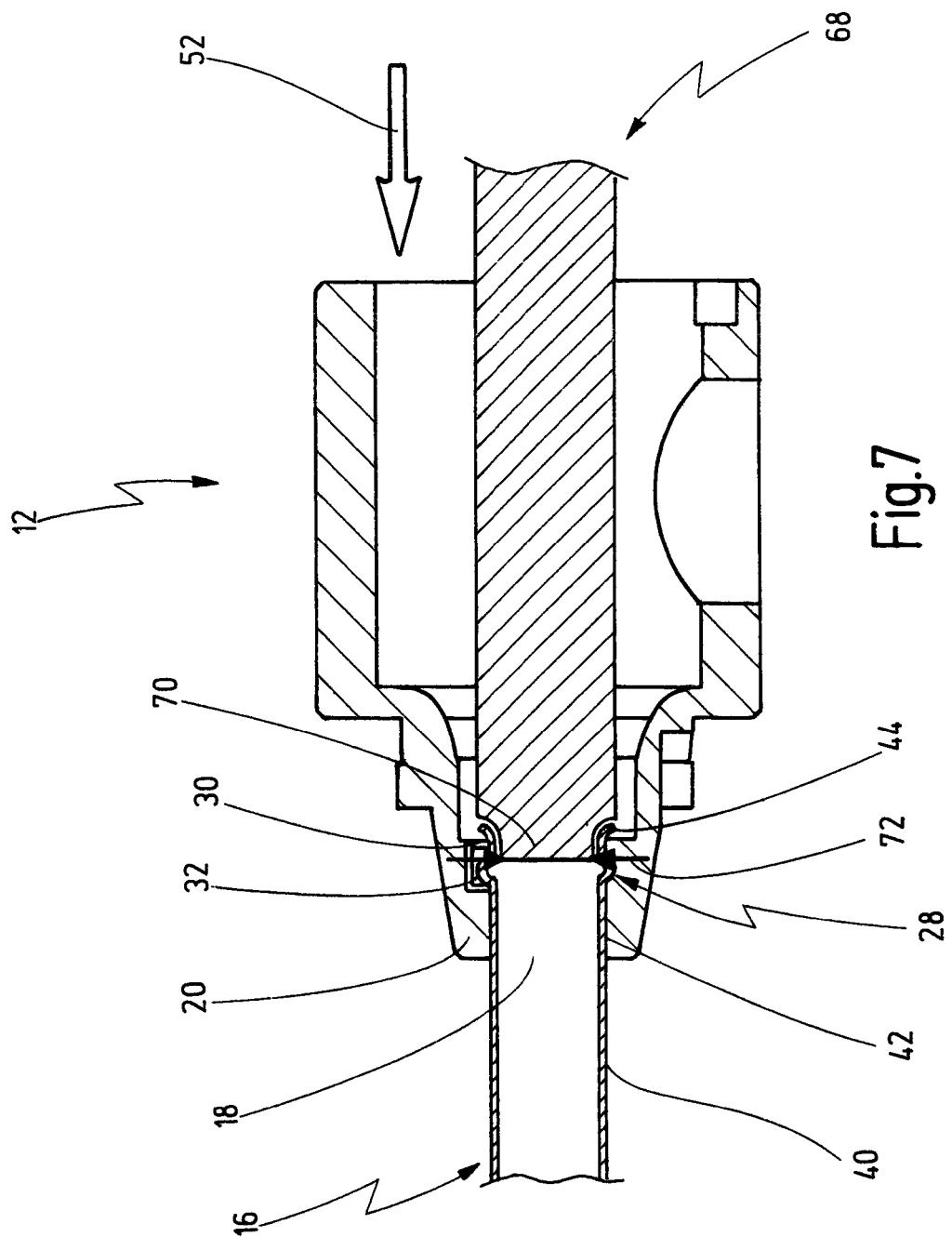
FIG. 7 shows the endoscope head and the optic tube from FIG. 6 and a further pressing tool in a further method step of the production method.

As is shown in FIG. 7, the proximal end 44 of the optic tube 16 is also widened in a trumpet shape, such that the external diameter 34 of the optic tube 16 increases at this location. The proximal end 44 of the optic tube 16 points outwards and away from a longitudinal axis of the optic tube 16. For this purpose, the pressing tool 54 is removed from the optic tube 16 and from the endoscope head 12. A further pressing tool 68 is pushed, in the direction of the arrow 52, through the endoscope head 12 and into the pressed-on optic tube 16, and it exerts an axial force on the proximal end area 18 of the optic tube 16.

The further pressing tool 68 likewise narrows at the distal end, although the narrowing is not in the form of a step shape but instead extends over a concavely curved partial area of a distal end 70. The smallest external diameter 72 of the distal end 70 of the further pressing tool 68 is also slightly smaller than the internal diameter 62 of the optic tube 16. The narrowing distal end 70 of the further pressing tool 68 spreads the proximal end 44 of the optic tube 16 outwards in such a way that a shape of the proximal end 44 of the optic tube 16 adapts to a shape of the distal end 70 of the further pressing tool 68. The pressing tool 54 and the pressing tool 68 can also be designed as one pressing tool, with which it is possible both to axially compress the proximal end area 18 of the optic tube 16 and also to widen the proximal end 44 of the optic tube 16.

During subsequent insertion of optical fibres into the endoscope 10, the widened proximal end 44 of the optic tube 16 avoids damage to said optical fibres.

Figure 8:
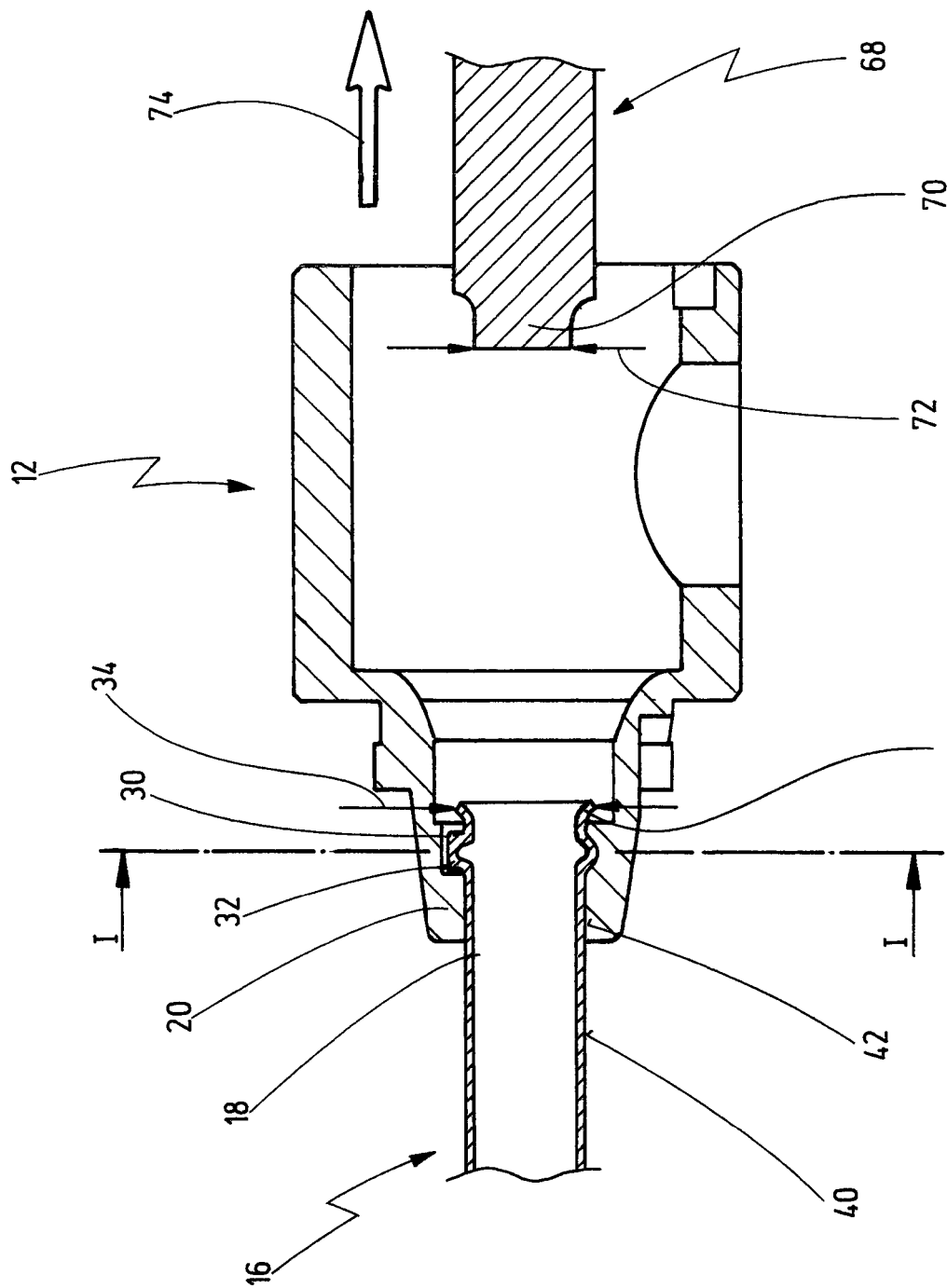
FIG. 8 shows the endoscope head, the optic tube and the further pressing tool from FIG. 7 in a further method step of the production method.

Thereafter, the further pressing tool 68 is removed from the endoscope head 12 in the direction of an arrow 74 (see FIG. 8).

After the pressing operation, the proximal end area 18 of the optic tube 16 is also adhesively bonded to the distal end area 20 of the endoscope head 12. For this purpose, an adhesive is applied to the outer surface 40 of the optic tube 16 and/or to the inner surface 42 of the distal end area 20 of the endoscope head 12. The adhesive bonding of the optic tube 16 to the endoscope head 12 serves to seal off the connecting site of the two endoscope parts from external influences, such as water.

Figure 9:
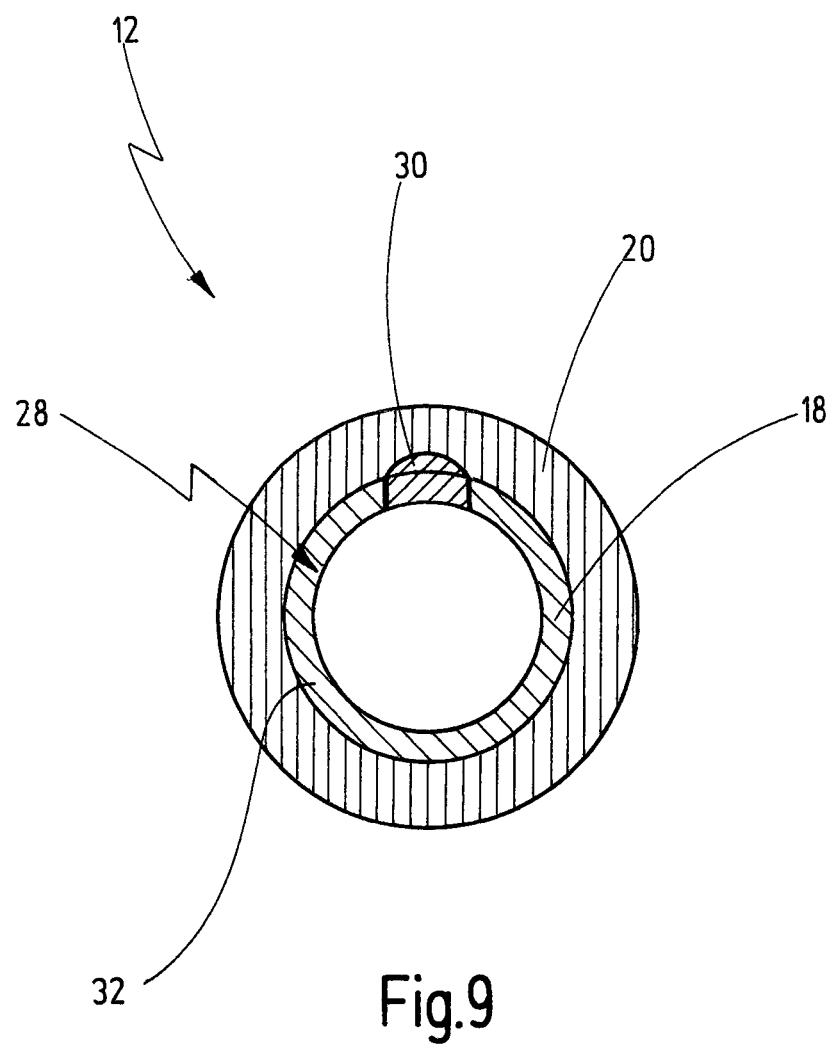
FIG. 9 shows the endoscope head in a cross section along the line I-I in FIG. 8.

FIG. 9 shows a cross-sectional view of the distal end area 20 of the endoscope head 12 along the line I-I in FIG. 8. The proximal end area 18 of the optic tube 16 is press-fitted with the distal end area 20 of the endoscope head 12. Material of the optic tube 16 engages with a form fit in the recess 28, formed as a groove 32 extending about the full circumference, and into the cavity 30.

The invention claimed is:

1. A method for producing an endoscope, comprising:
providing an endoscope head having a distal end area with a circumferential groove and a circumferentially limited cavity extending only over a part of a circumference of the distal end area of the endoscope head, the circumference defined about a longitudinal axis of the endoscope;
providing an optic tube;
inserting a proximal end area of the optic tube into the distal end area of the endoscope head, wherein an external diameter of the optic tube is slightly smaller than an internal diameter of the distal end area of the endoscope head; and
axially compressing the proximal end area of the optic tube in a manner that widens the proximal end area of the optic tube and thereby causes an interference fit between the proximal end area of the optic tube and the distal end area of the endoscope head, wherein, during the axially compressing step, an axial force is exerted on the proximal end area of the optic tube in a direction toward a distal end area of the optic tube;
wherein, during the axially compressing step, material of the optic tube flows into the circumferential groove of the endoscope head to define a form fit therewith, and material of the optic tube engages in the circumferentially limited cavity such that the optic tube is not able to turn relative to the endoscope head about the longitudinal axis of the endoscope head.

2. The method of claim 1, wherein the axial force is provided by a pressing tool.

3. The method of claim 1, further comprising widening a proximal end of the optic tube to define a trumpet shape.

4. The method of claim 3, further comprising, after the axially compressing step, adhesively bonding the distal end area of the endoscope head to the proximal end area of the optic tube.

5. The method of claim 1, wherein the inserting step involves inserting the proximal end area of the optic tube into a bore defined by the distal end area of the endoscope head;
wherein the bore extends along a bore axis and includes a distal bore portion defined by a distal bore surface, and a proximal bore portion defined by a proximal bore surface;
wherein the bore defines the circumferential groove between the distal bore portion and the proximal bore portion; and
wherein a first radial distance between the bore axis and the distal bore surface has a same magnitude as a second radial distance between the bore axis and the proximal bore surface.

6. The method of claim 5, wherein the bore further defines the circumferentially limited cavity between the distal bore portion and the proximal bore portion.

7. The method of claim 6, wherein a third radial distance between the bore axis and a surface defining the circumferentially limited cavity has a magnitude greater than a magnitude of the second radial distance between the bore axis and the proximal bore surface; and
wherein the magnitude of the third radial distance between the bore axis and the surface defining the circumferentially limited cavity is greater than a magnitude of a fourth radial distance between the bore axis and a surface defining the circumferential groove.

8. The method of claim 7, wherein the compressing step involves exerting the force using a pressing tool that has been inserted through the endoscope head in a direction from a proximal end area of the endoscope head toward the distal end area of the endoscope head; and
wherein, in a fully inserted state of the pressing tool, a distal end of the pressing tool extends past the circumferentially limited cavity and is received within the optical tube.

9. A method for producing an endoscope, comprising:
providing an optic tube;
providing an endoscope head having a distal end area with a circumferential groove and a circumferentially limited cavity extending only over a part of a circumference of the distal end area of the endoscope head, the circumference defined about a longitudinal axis of the endoscope;
inserting a proximal end area of the optic tube into a distal end area of the endoscope head, wherein an external diameter of the optic tube is slightly smaller than an internal diameter of the distal end area of the endoscope head; and
axially compressing the proximal end area of the optic tube in a manner that widens the proximal end area of the optic tube and thereby causes an interference fit between the proximal end area of the optic tube and the distal end area of the endoscope head;
wherein, during the axially compressing step, material of the optic tube flows into the circumferential groove of the endoscope head to define a form fit therewith, and material of the optic tube engages in the circumferentially limited cavity such that the optic tube is not able to turn relative to the endoscope head about the longitudinal axis of the endoscope head.

10. The method of claim 9, wherein the inserting step involves inserting the proximal end area of the optic tube into a bore defined by the distal end area of the endoscope head.

11. The method of claim 10, wherein the axially compressing step involves exerting a force on the proximal end area of the optic tube in a direction of the longitudinal axis of the optic tube.

12. The method of claim 11, wherein the axially compressing step involves exerting the force using a pressing tool that has been guided through the endoscope head in a direction from the proximal end area of the endoscope head toward the distal end area of the endoscope head.

13. The method of claim 12, wherein the axially compressing step involves forcing the proximal end area of the optic tube radially outward relative to the longitudinal axis of the optic tube.

14. The method of claim 12, further comprising a step of widening the proximal end of the optic tube relative to another portion of the proximal end area of the optic tube.

15. The method of claim 10, wherein the bore extends along a bore axis and includes a distal bore portion defined by a distal bore surface, and a proximal bore portion defined by a proximal bore surface;
   wherein the bore defines the circumferential groove between the distal bore portion and the proximal bore portion; and
   wherein a first radial distance between the bore axis and the distal bore surface has a same magnitude as a second radial distance between the bore axis and the proximal bore surface.

16. The method of claim 15, wherein the bore further defines the circumferentially limited cavity between the distal bore portion and the proximal bore portion.

17. The method of claim 16, wherein a third radial distance between the bore axis and a surface defining the circumferentially limited cavity has a magnitude greater than a magnitude of the second radial distance between the bore axis and the proximal bore surface; and
   wherein the magnitude of the third radial distance between the bore axis and the surface defining the circumferentially limited cavity is greater than a magnitude of a fourth radial distance between the bore axis and a surface defining the circumferential groove.

18. The method of claim 17, wherein the axially compressing step involves exerting a force using a pressing tool that has been inserted through the endoscope head in a direction from the proximal end area of the endoscope head toward the distal end area of the endoscope head; and
   wherein, in a fully inserted state of the pressing tool, a distal end of the pressing tool extends past the circumferentially limited cavity and is received within the optical tube.

19. A method for producing an endoscope, comprising:
   providing an endoscope head having a distal end area with a bore that extends along a bore axis, the bore including:
      a proximal bore portion defined by a proximal bore surface, and a distal bore portion defined by a distal bore surface, wherein a first radial distance between the bore axis and the distal bore surface has a same magnitude as a second radial distance between the bore axis and the proximal bore surface;
      a groove between the proximal bore portion and the distal bore portion, the groove extending over an entirety of a circumference defined about a longitudinal axis of the endoscope; and
      a cavity between the proximal bore portion and the distal bore portion, the cavity extending over only a portion of the circumference;
   providing an optic tube with an external diameter that is slightly smaller than an internal diameter of the bore;
   inserting a proximal end area of the optic tube into the bore; and
   axially compressing the proximal end area of the optic tube in a manner that widens the proximal end area of the optic tube and thereby causes an interference fit between the proximal end area of the optic tube and the bore, wherein, during the axially compressing step, an axial force is exerted on the proximal end area of the optic tube in a direction toward a distal end area of the optic tube;
   wherein, during the axially compressing step, material of the proximal end area of the optic tube flows into the groove of the endoscope head to define a form fit therewith, and material of the proximal end area of the optic tube engages in the cavity such that the optic tube is not able to turn relative to the endoscope head about the longitudinal axis of the endoscope head.

20. The method of claim 19, wherein a third radial distance between the bore axis and a surface defining the cavity has a magnitude greater than a magnitude of the second radial distance between the bore axis and the proximal bore surface; and
   wherein the magnitude of the third radial distance between the bore axis and the surface defining the cavity is greater than a magnitude of a fourth radial distance between the bore axis and a surface defining the groove.

* * * * *